US006224560B1

(12) United States Patent
Gazula et al.

(10) Patent No.: US 6,224,560 B1
(45) Date of Patent: May 1, 2001

(54) FLOW RESTRICTOR FOR MEASURING RESPIRATORY PARAMETERS

(75) Inventors: Gopala Krishna Murthy Gazula, Somerville; John J. Godleski, Weston, both of MA (US)

(73) Assignee: Harvard: The President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/151,914

(22) Filed: Sep. 11, 1998

(51) Int. Cl.[7] .................................................. A61B 5/08

(52) U.S. Cl. ..................... 600/538; 600/529; 600/300; 128/128; 128/204.23

(58) Field of Search ................................ 600/529–538, 600/300–301; 128/897–898, 204.12–204.25

(56) References Cited

U.S. PATENT DOCUMENTS

| 5,134,890 | * | 8/1992 | Abrams | 600/538 |
| 5,287,851 | * | 2/1994 | Beran et al. | 128/204.23 |
| 5,347,843 | * | 9/1994 | Orr et al. | 600/538 |
| 5,454,375 | * | 10/1995 | Rothenberg | 600/538 |
| 5,676,132 | * | 10/1997 | Tillotson et al. | 600/537 |

* cited by examiner

Primary Examiner—Cary O'Connor
Assistant Examiner—Michael Astorino
(74) Attorney, Agent, or Firm—Perkins, Smith & Cohen, LLP; Jacob N. Erlich; Jerry Cohen

(57) ABSTRACT

A flow restrictor is applied to a respiration-channeling device such as a tracheostomy tube, a mouthpiece, or a face mask. The flow restrictor creates a pressure differential which varies with volume flow rate. A pressure reading is taken on either side of the flow restrictor in the respiration-channeling device and from this, a volume flow rate is determined. A data acquisition device is used to derive further pulmonary function parameters from the volume flow rate.

21 Claims, 10 Drawing Sheets

| Time (min) | Ti (s) | Te (s) | PIF (cc) | PEF (cc) | TV (cc) | f | MV (cc/min) | RT (s) | EIP (ms) | EEP (ms) | PAU |
|---|---|---|---|---|---|---|---|---|---|---|---|
| 3.13 | 1.276 | 1.491 | 417.5 | 415.4 | 393.8 | 21.77 | 8545 | 0.9131 | 133.1 | 80.18 | 0.6416 |
| 5.1 | 1.245 | 1.562 | 345.6 | 379.2 | 323.4 | 21.46 | 6940 | 0.8179 | 136.4 | 164.4 | 0.9194 |
| 7.13 | 1.218 | 1.461 | 339.4 | 371 | 304.3 | 22.53 | 6809 | 0.7864 | 134 | 126 | 0.8921 |
| 9.13 | 1.271 | 1.519 | 303.8 | 338.7 | 278.3 | 21.8 | 5985 | 0.7644 | 148.4 | 170.9 | 1.014 |
| 11.1 | 1.343 | 1.839 | 300.3 | 300.7 | 302.8 | 19.42 | 5873 | 0.9834 | 116.8 | 412 | 0.9099 |
| 13.12 | 1.317 | 1.598 | 313.8 | 317 | 305.5 | 20.73 | 6270 | 0.8895 | 112.9 | 129.1 | 0.8181 |
| 15.12 | 1.298 | 1.714 | 259.6 | 274.7 | 248.4 | 20.15 | 4975 | 0.8583 | 117.9 | 325.4 | 1 |
| 17.1 | 1.352 | 1.778 | 285.7 | 279.4 | 285.2 | 19.31 | 5511 | 0.9458 | 117 | 276.5 | 0.9062 |
| 19.1 | 1.413 | 2.02 | 244.8 | 250.1 | 248.6 | 17.84 | 4450 | 0.9357 | 108.8 | 455.5 | 1.179 |
| 21.15 | 1.339 | 3.038 | 243.9 | 263.5 | 239 | 17.83 | 4295 | 0.8783 | 121.5 | 685.8 | 2.363 |
| 23.1 | 1.348 | 2.05 | 245.6 | 256.2 | 234.4 | 19.15 | 4450 | 0.8458 | 119.4 | 656 | 1.457 |
| 25 | 1.403 | 2.86 | 241.9 | 263 | 244.6 | 16.58 | 4046 | 0.8927 | 119 | 1185 | 2.132 |
| 27.1 | 1.448 | 2.19 | 262.7 | 266.3 | 271.5 | 18.2 | 4886 | 0.9727 | 130.4 | 282.7 | 1.327 |
| 29.15 | 1.514 | 5.333 | 237.4 | 249 | 257 | 15.62 | 4009 | 1.003 | 110.6 | 2356 | 4.509 |
| 31.13 | 1.446 | 3.004 | 255.5 | 251.4 | 258.8 | 16.3 | 4161 | 1.019 | 110.8 | 695.6 | 1.857 |
| Average | 1.3487 | 2.2305 | 286.5 | 298.37 | 279.71 | 19.25 | 5414 | 0.9004 | 122.467 | 533.4053 | 1.461687 |
| St.Dev. | 0.0831 | 1.0166 | 51.1059 | 53.886 | 41.98 | 2.166 | 1319 | 0.07741 | 11.4522 | 585.927 | 0.983217 |

Measurements are 2 minute averages.

Table of Breathing Parameters of an Adult Human Female Subject

FIG. 8

FLOW RESTRICTOR FOR MEASURING RESPIRATORY PARAMETERS

STATEMENT OF GOVERNMENT INTEREST

This invention was partially funded by the Government under a grant from the National Institute of Health and NIEHS. The Government has certain rights in portions of the invention.

FIELD OF THE INVENTION

This invention relates generally to medical devices and more particularly to medical devices for measuring respiratory parameters.

BACKGROUND OF THE INVENTION

When measuring pulmonary function, as in medical and experimental physiological testing on humans or animals, it is desirable to measure lung function by monitoring respiratory patterns.

Existing methods of measuring respiratory parameters include placing an expandable tube around the chest of a human or animal subject. As the subject breathes, the tube lengthens and relaxes as the subject's chest expands and contracts. Strain gauges on the tube are used to determine the volume of expansion of the subject's chest and, from this, a volume of air flow can be derived. A disadvantage of this method is that it only indirectly measures a limited number of parameters. The strain gauge method measures breathing frequency and time for inspiration and time for expiration, but yields no direct measurement of air flow. In addition, the tube may easily come loose, or dislodge completely, causing the measurement quality to deteriorate. In particular, animal subjects, such as dogs, find the tube annoying and they contribute to the loosening and displacement by trying to remove the tube.

Another existing method of measuring respiratory parameters is a magnetometry device. Magnetometry devices are placed on the chest of the subject to measure respiratory parameters. These devices, however, like the strain gauge/tubing devices, measure only limited parameters, and do not directly measure air flow.

A third existing method for measuring respiratory parameters is the whole body plethysmograph, also called a pressure plethysmograph. In this method, the subject is placed inside a box. As the subject in the box breathes and moves air, the changes in the volume and the air flows in the box are measured. Like the methods disclosed above, this method provides only a indirect measure of air flow. It is also somewhat inaccurate. This method cannot be used as a bedside device to monitor the respiratory parameters of someone who is seriously ill, such as those who are anesthetized, in a coma, or in intensive care because they must be able to follow commands. Lastly, the accuracy of the whole body method is limited.

A fourth existing method for measuring respiratory parameters is the spirometer, which works on the basic principle of changing the volume of gas in a container using respiration. The spirometer may be used to measure all the breathing patterns which the devices described above measure. The spirometer, however, is difficult to use on unanesthetized animals. Further, the spirometer cannot be used for exposure experiments, i.e. to introduce gases or particulates, or in clinical situations, i.e. in surgery or emergency situations. In addition, the spirometers available commercially today tend to be expensive compared to other methods of measuring respiratory parameters.

It is an object of the present invention to provide a method and apparatus to measure respiratory parameters directly.

It is another object of the present invention to provide a method and apparatus to measure respiratory parameters as compactly and comfortably as possible in both humans and animals.

It remains desirable to have a means for measuring respiratory parameters accurately and conveniently with a minimum of discomfort to and input from the human or animal subject.

SUMMARY OF THE INVENTION

The problems of accurately measuring respiratory parameters are solved by the present invention of a flow restrictor device and method for measuring respiratory parameters.

A flow restrictor is applied to a respiration-channeling device such as a face mask, a mouthpiece, or a tracheostomy tube. The flow restrictor creates a pressure differential which varies with volume flow rate. A pressure reading is taken on either side of the flow restrictor in the respiration-channeling device and from this, a volume flow rate is determined. A data acquisition device is used to derive further pulmonary function parameters from the volume flow rate.

The flow restrictor device works regardless of the subject's position, i.e. the subject may be sitting up or lying down. Therefore, although not limited thereto, the device can be used on non-responsive patients and non-compliant experimental animal subjects.

The present invention together with the above and other advantages may best be understood from the following detailed description of the embodiments of the invention illustrated in the drawings, wherein:

BRIEF DESCRIPTION OF THE DRAWINGS

FIG. 8 is a table of data gathered on a normal adult human female using the present invention with the preferred embodiment of the face mask; and, FIG. 9 is a series of bar graphs showing the results of sleep apnea studies on dogs using an embodiment of the present invention.

DETAILED DESCRIPTION OF PREFERRED EMBODIMENTS

Figure 1:
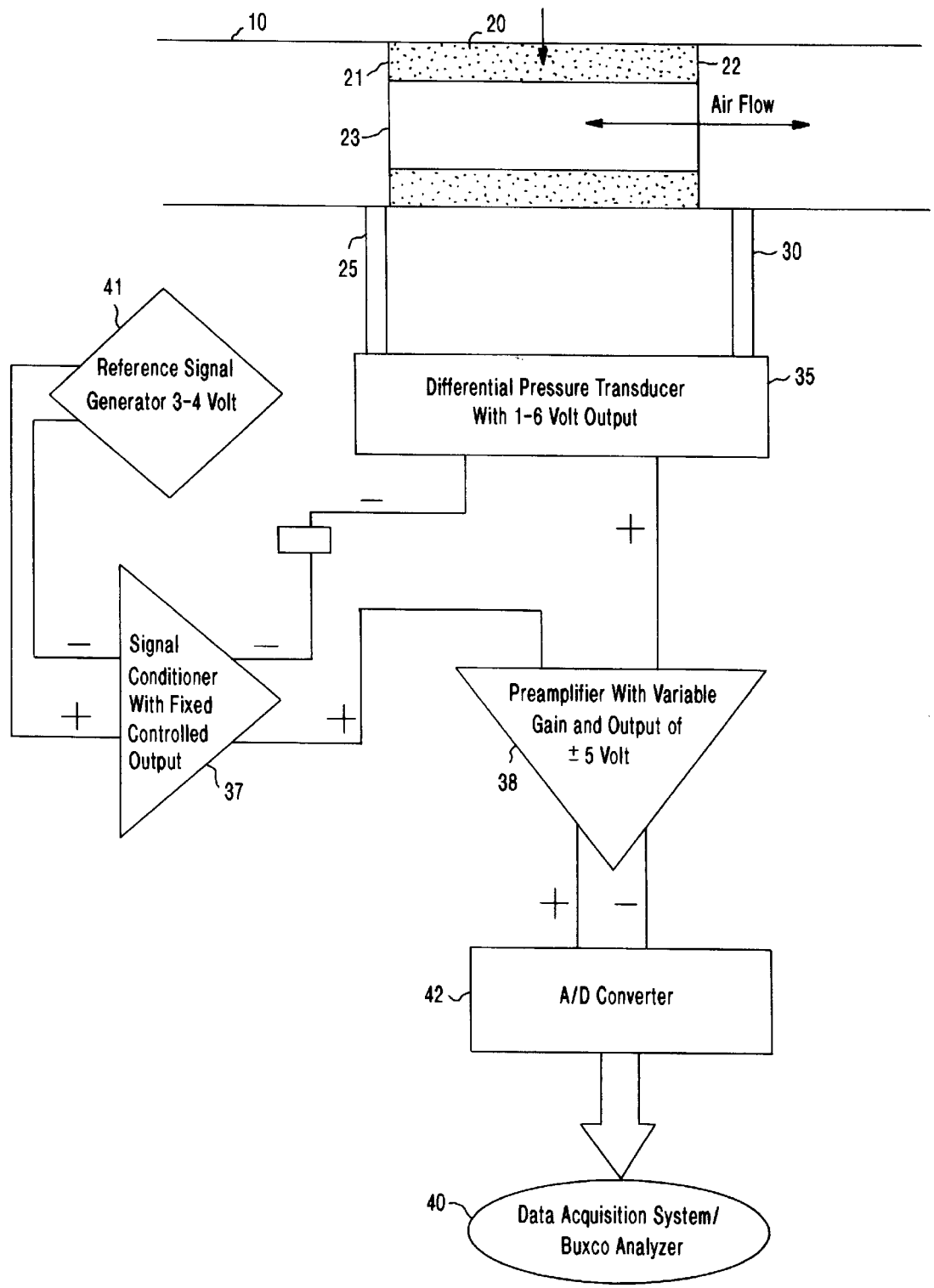
FIG. 1 is a schematic diagram of a flow restrictor and data acquisition system according to principles of the invention.

FIG. 1 is a schematic drawing of a generic embodiment of an apparatus having a flow restrictor and associated electronics for data gathering for measuring respiratory parameters according to the principles of the invention. Respiratory pattern measurements are carried out by measuring the volume flow rate of inhalation and exhalation through a breathing tube 10 which is attached at a first end to a human or animal subject (not shown). A second end of the breathing tube 10 is connected to a source of air. The subject breathes through the breathing tube 10 which acts as a respiration-channeling device.

A flow restrictor 20 is positioned inside the breathing tube 10. The flow restrictor 20 has a first end 21 and a second end 22 and an opening 23. The flow restrictor opening 23 has a diameter which is for example 6.44 mm. The outer wall of the flow restrictor 20 is formed and dimensioned to engage with the inner wall of the breathing tube 10 so that substantially all air flow in the breathing tube 10 flows through the flow restrictor opening 23. In the present embodiment of the invention, the outer wall of the flow restrictor 20 is tapered so that the flow restrictor 20 may be press fit into the breathing tube 10. The dimensions of the flow restrictor 20 should be such that an accurate pressure measurement may be made, but the diameter of the flow restrictor opening 23 may not be so small that the subject has difficulty breathing. The relative sizes of the breathing tube 10, the flow restrictor 20, and the size of the flow restrictor opening 23 will depend on the size of the subject, human or animal.

A first pressure-sensor tube 25 is positioned to take a measurement of air pressure in the breathing tube 10 at the first end 21 of the flow restrictor 20. A second pressure-sensor tube 30 is positioned to take a measurement of air pressure at the second end 22 of the flow restrictor 20. The first 25 and second 30 pressure-sensor tubes may be for example 1.7 mm in diameter. The pressure-sensor tubes 25, 30 may be manufactured from any material suitable for medical devices, however the material should preferably be a lightweight material to avoid excessive weight being attached to the breathing tube 10 in order to make the apparatus as light and comfortable for the subject as possible.

The first pressure-sensor tube 25 may alternatively be positioned in the breathing tube 10 at the first end 21 of the flow restrictor 20 so that it does not connect through the breathing tube wall but rather through the flow restrictor wall. The second pressure sensor tube may also be run through the flow restrictor wall.

The first 25 and second 30 pressure-sensor tubes are connected to a differential pressure transducer 35. The present invention is a modified venturi tube, as will be explained below, and operates on the principle that a flow restriction in a pipe causes a pressure drop in the flow through the pipe which varies with flow rate. Thus, the pressure differential detected by the pressure transducer 35 yields a value for the volume flow rate of the subject's breathing.

The differential pressure transducer 35 is connected to a data acquisition system 40 through signal modifying electronics. The data acquisition system 40 collects data provided by the pressure transducer 35 continuously, making analysis possible for each breath over a data collection period. In the present embodiment of the invention, the pressure transducer 35 is a bipolar pressure transducer available from Omega Engineering of Stamford, Conn., although other pressure transducers may be used in the present invention. The output of the pressure transducer 35 is 1–6 volts. When the differential pressures are −63 mm water to +63 mm water, the outputs are 1 volt and 6 volts, respectively. These output signals are supplied to the data acquisition system 40, such as a BUXCO system which is PC-based and includes data analysis software. The BUXCO system is available from BUXCO Electronics Inc., Troy, N.Y. This acquisition system 40 needs a bi-polar signal input. To supply this type of input, a signal conditioner 37 and a preamplifier 38 are added to the circuit. The signal conditioner 37 generates an output substantially equal to the differential pressure transducer 35 output (+3.5 volts) when the pressure differential equals 0 mm water. The output signal of the pressure transducer 35, after modifying using the signal conditioner 37 and a reference signal generator 41, is −2.5 volts for a pressure of −63 mm water and +2.5 volts for a pressure of +63 mm water, inhalation and exhalation respectively. The design, however, is such that the pressure drop across the flow restrictor 20 does not generally exceed ±10 mm water, giving an output signal of ±0.50 volts. The pre-amplifier circuit 38 is designed to amplify the signal to ±5 volts. The pre-amplifier 38 may be purchased from American Advantech. The pre-amplifier 38 has capabilities to offset the signal by 50% and has several fixed gain settings in the range of 1–1000. The amplified signal is supplied to the data acquisition system 40 through an analog to digital converter 42.

Figure 2:
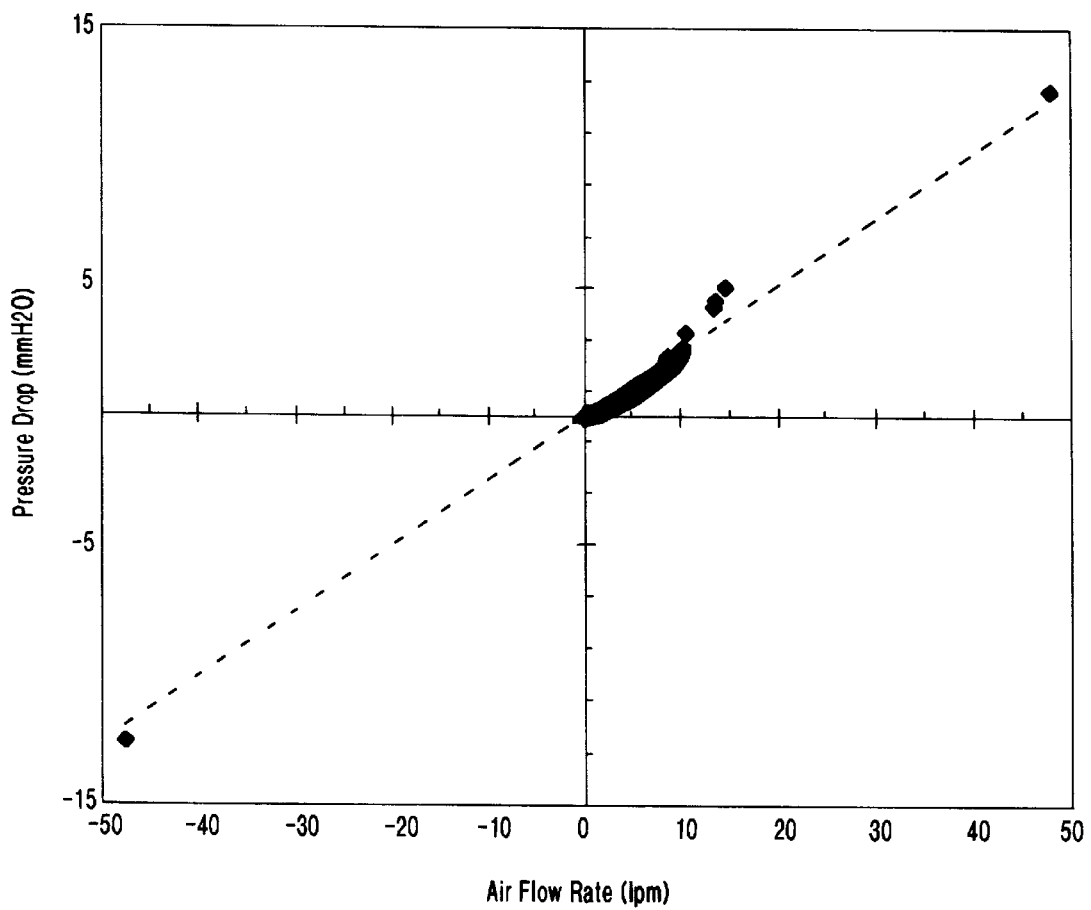
FIG. 2 is a graph of the pressure drop across the flow restrictor as a function of the air flow rate through the flow restrictor for a preferred embodiment of the invention.

FIG. 2 is a calibration graph of the pressure drop across the flow restrictor as a function of the air flow rate through the restrictor. The flow restrictors are calibrated between the low and high expected flow points before each experiment. Venturi meters and orifice meters measure the average flow rates by measuring the pressure differential across a calibrated resistance in the flow stream. For a venturi meter, pressure is measured upstream and at the venturi throat. The flow-pipe, upstream and downstream of the venturi, is kept long enough to maintain a laminar flow. The upstream pipe cross-sectional area ($A_1$) is about 3–5 times larger than the throat cross-sectional area ($A_2$). The differential pressure will depend on the ratio ($A_1/A_2$) and the flow rate. These physical dimensions allow the flow in the breathing tube 10 to be laminar. For the flow measurements, the differential pressures are normally about 10 to 250 mm $H_2O$. Venturi and orifice flow meters are generally used for measuring the flows of the order of 50–1000 liters per minute. The embodiment for human subjects, described below, takes the typical flows for humans into account and accordingly the area ratio ($A_1/A_2$) is altered to maintain a similar pressure differential. For humans, the normal volume is 6–8 liters per minute, and under stress, 20 liters per minute. For dogs, the air flows during normal breathing conditions are approximately 0.5 to 1 liters per minute and may reach over 15 liters per minute when the dogs are panting.

The present invention incorporates the following design factors for humans and animals in order to accomplish the best device for the intended application:

1. no modifications to the breathing tube
2. no substantial weight added to the breathing assembly
3. no alteration to the particles and gases channeled through the flow-restrictor, and
4. a compact and comfortable assembly for both human and animal subjects.

Figure 3A:
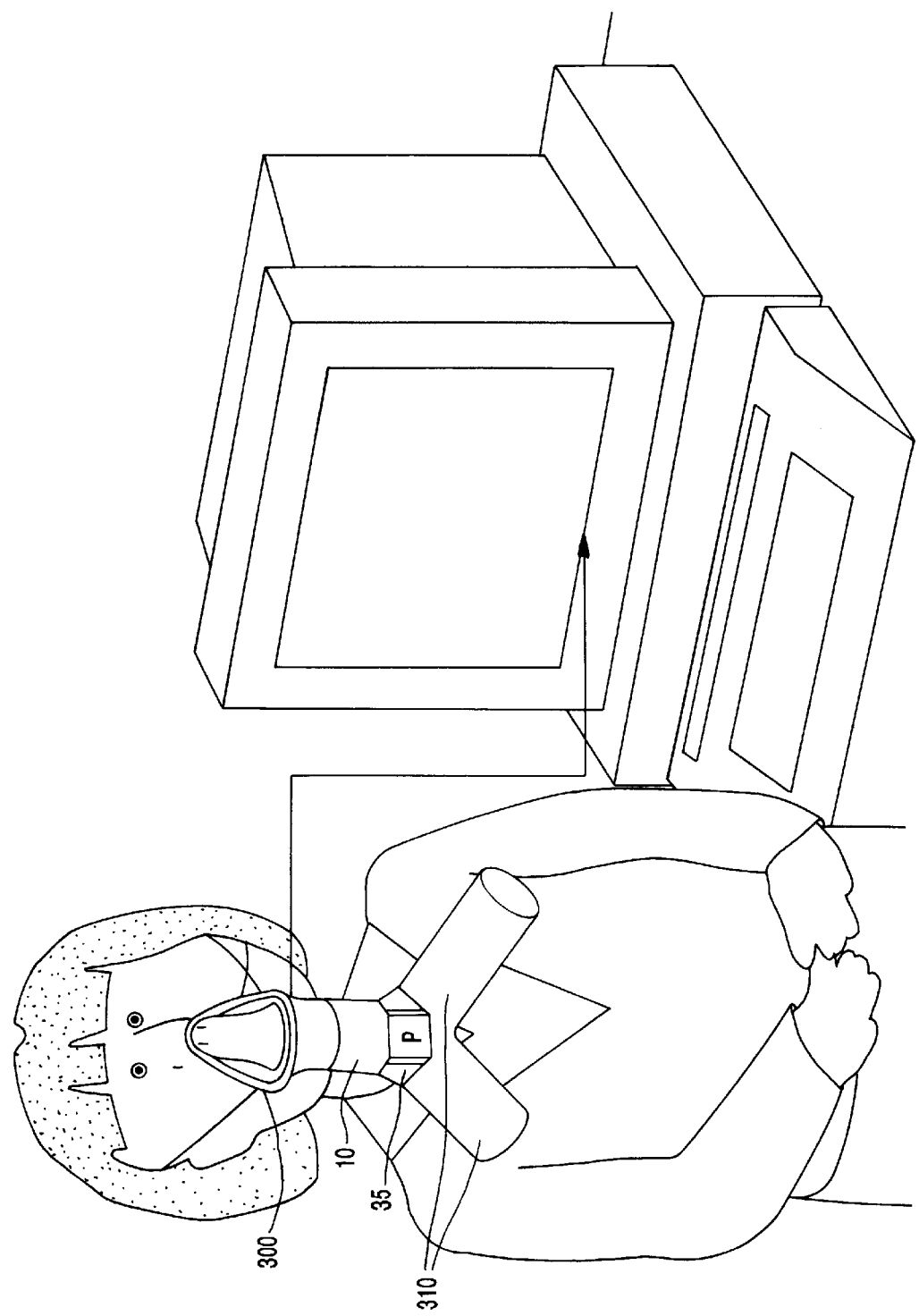
FIG. 3a is a drawing of a human subject using a first alternative preferred embodiment of the invention.

FIG. 3a is a drawing of a human subject using a first alternative embodiment of the present invention. The subject breathes through a mask 300 connected to the breathing tube 10 which has a flow restrictor 20. An arrangement of Y-tubes 310 allows air to be taken in and exhausted away from the breathing tube 10. The pressure transducer 35 is mounted to the air flow tubes 310.

Figure 3B:
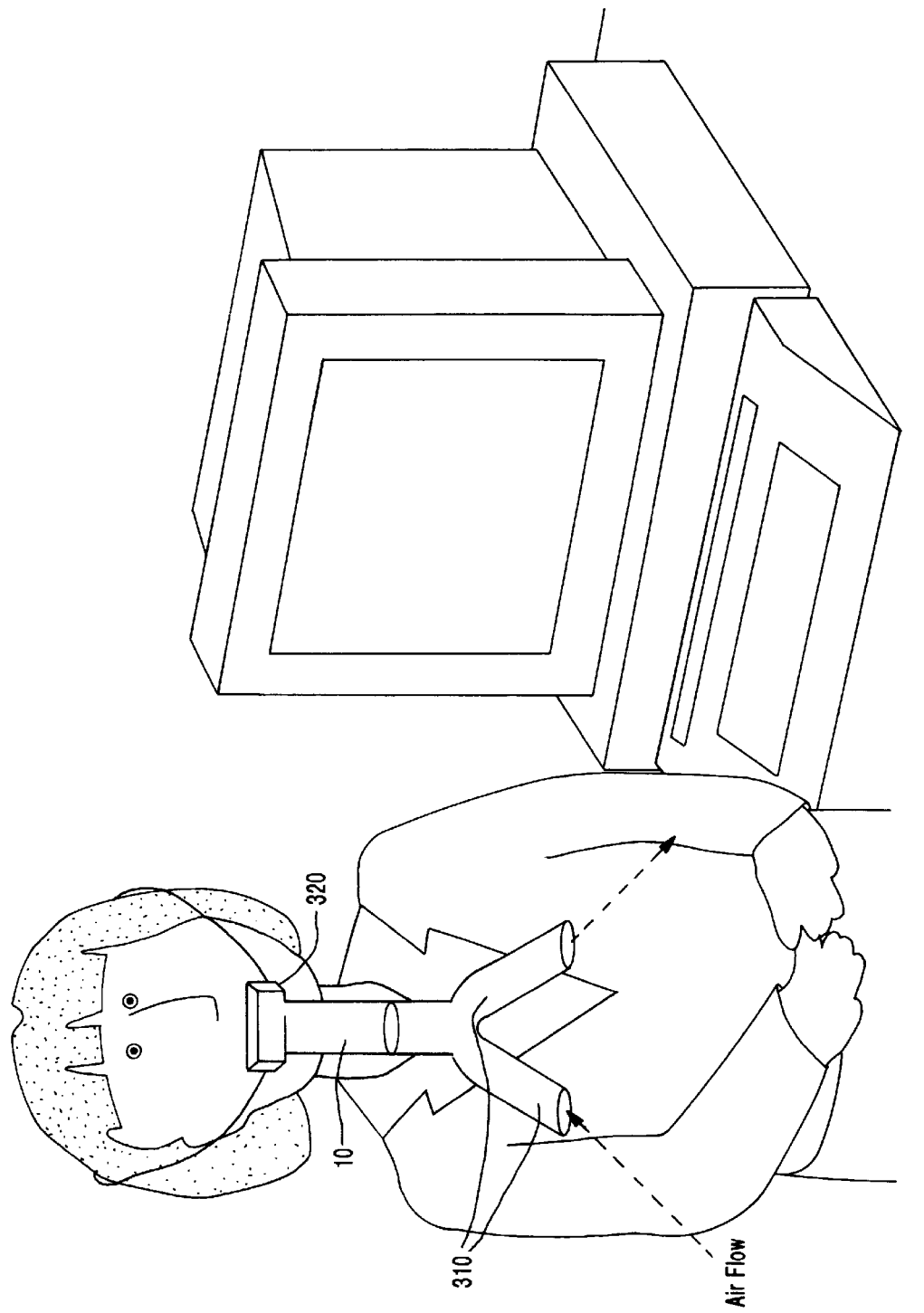
FIG. 3b is a drawing of a human subject using a second alternative preferred embodiment of the invention.

FIG. 3b is a drawing of a human subject using a second alternative embodiment of the present invention. The subject breathes through a mouthpiece 320 connected to the breathing tube 10 which has a flow restrictor 20. An arrangement of Y-tubes 310, like those shown in FIG. 3a, allows air to be taken in and exhausted away from the breathing tube 10.

Figure 4:
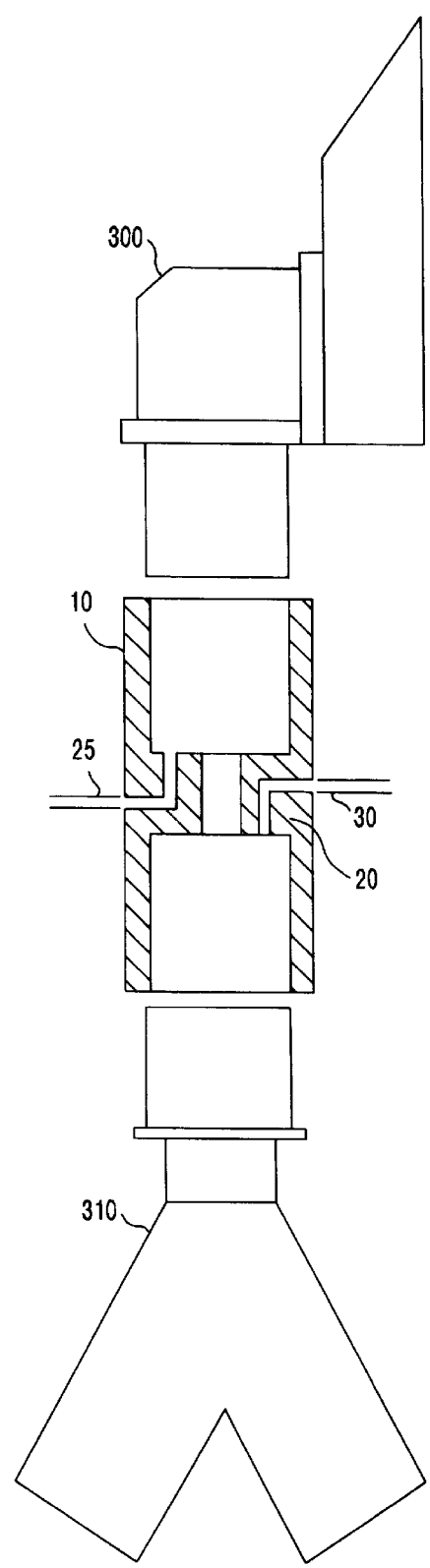
FIG. 4 is a part schematic/part cross-sectional view of the flow restrictor according to principles of the present invention in the first alternative preferred embodiment of the invention of FIG. 3.

FIG. 4 is a part schematic/part cross-sectional view of the first alternative embodiment of the flow restrictor to be applied to human subjects shown in FIG. 3. In this alternative embodiment of the invention, the flow restrictor 20 is used in conjunction with a mask device 300 which is positioned over the nose of a subject. In this embodiment, the subject breathes through the nose. The mask 300 is attached to the breathing tube 10 which has a flow restrictor 20 inside it. Two pressure sensor tubes 25, 30, one positioned at each side of the flow restrictor 20, are used to sense the pressure difference across the flow restrictor 20 as described for the generic embodiment above. The breathing tube 10 is connected to Y-adapter 310 for air intake and exhaust. The Y-adapter 310 may be connected to hoses to feed specific gas mixtures including gases with particulates to the subject for therapy or for testing.

Figure 5:
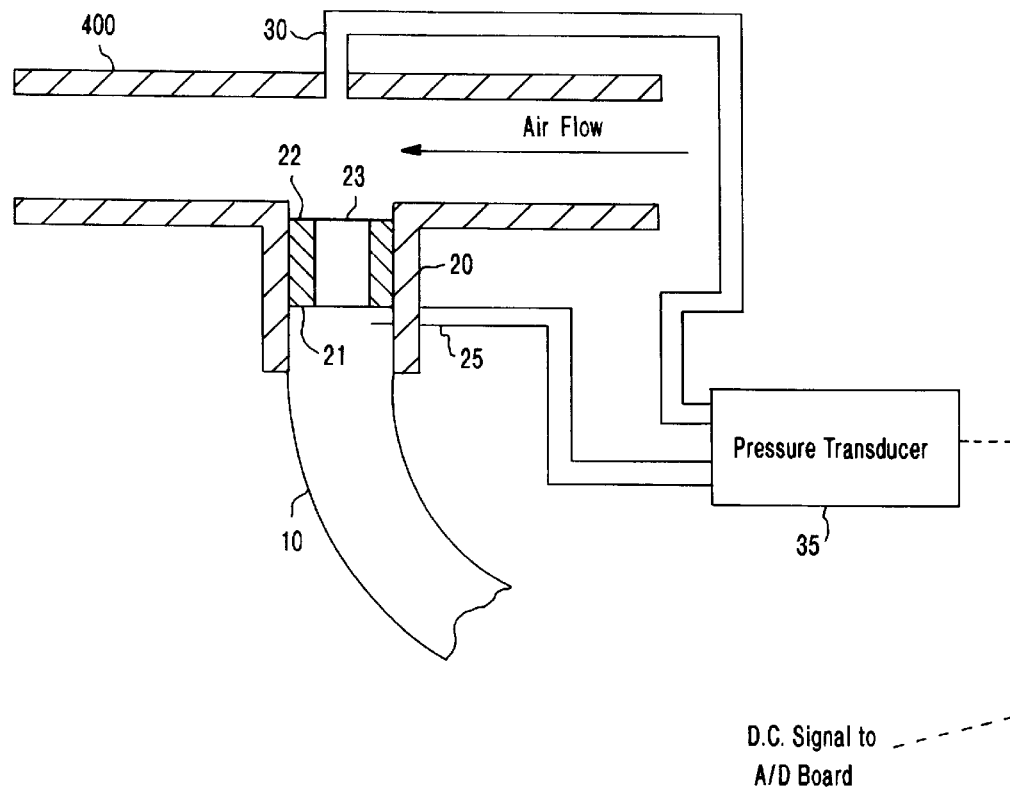
FIG. 5 is a schematic view of a third alternative preferred embodiment of the flow restrictor to be applied to animals such as dogs.

FIG. 5 shows a third alternative embodiment which is for dogs and other animals. In conscious animals, particularly in controlled and lengthy lab experiments, a tracheostomy offers an advantage over a face mask. FIG. 5 shows the breathing tube 10 with the flow restrictor 20. Here the breathing tube 10 is also a tracheostomy tube. The tracheostomy tube is attached to a dog at one end and is connected to a T-connector 400 at the other. The T-connector 400 may be connected to hoses to introduce specific gases mixtures. The flow restrictor design takes the dimensions of the breathing tube 10 and the T-connector 400 into account. The area ratio ($A_1/A_2$) for the design is kept at a value of approx. 5 (five), which is within the typical range for venturi flow restrictors. A laminar flow is maintained across the restrictor, i.e. the value of Reynolds number, calculated based on minute volumes, is held at less than 2100.

Figure 6:
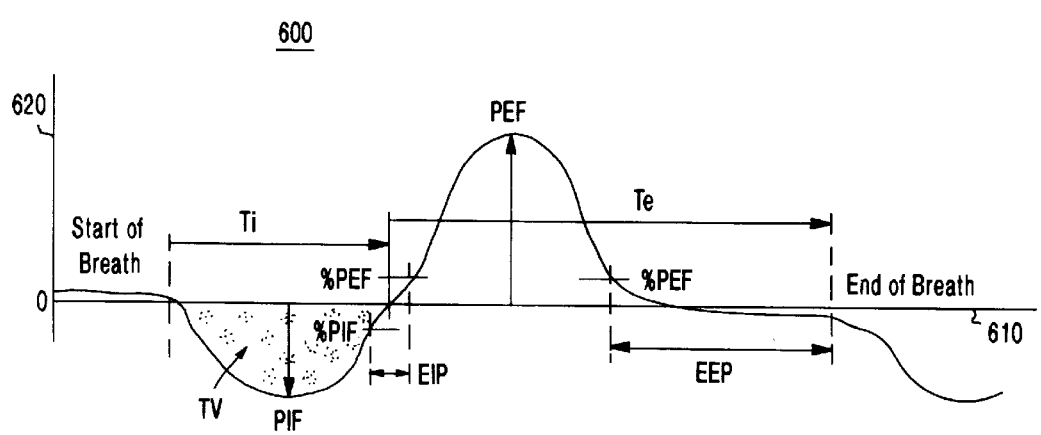
FIG. 6 is a volume flow rate vs. time trace generated by the data acquisition system using the present invention.

FIG. 6 shows a volume flow rate vs. time trace 600 generated by the data acquisition system 40 using the calibrated relationships between pressure and volume flow rate and signals from the preamplifier 37. The volume flow rate vs. time trace 600 is a sine wave-like curve on a graph where the x-axis 610 is time and the y-axis 620 is volume flow rate. The positive portion of the y-axis 620 represents exhalation values, and the negative portion of the y-axis 120 represents inhalation values.

The volume flow rate vs. time trace 600 may be used to derive a number of pulmonary function parameters. The volume flow rate vs. time trace indicates the volume flow rate of the subject's breath. From the volume flow rate, a number of other pulmonary function parameters are derived. The BUXCO program computes all the breathing parameters on a breath-by-breath basis for a user-provided criteria and reports the averages of each of the values every minute or other user-specified time periods.

The breathing parameters determined are as follows: time for inspiration ($T_i$); time for expiration ($T_e$); peak inspiratory flow (PIF); peak expiratory flow (PEF); tidal volume (TV); relaxation time (RT); minute ventilation (MV); breathing or respiratory frequency (f); end inspiratory pause (EIP); end expiratory pause (EEP); pause (PAU); and enhanced pause (Penh). The time for inspiration is the total time for one inspired period. The time for expiration is the total time for one expiration cycle. The tidal volume is the total volume inspired. The relaxation time is defined as the time of volume decay of the expiration volume (area under flow rate vs. time curve for expiration) to 70 percent (70% of TV expired). The minute ventilation is the total inspired volume over a period of one minute. The end inspiratory pause is the time measured from 20% of the PIF to the inspiration endpoint. The end expiratory pause is the time measured from 20% of the PEF to the expiration endpoint. Pause is the ratio PEF/PIF and is an indication of bronchoconstriction. Enhanced pause is a modified pause and is ((Te/RT−1) (PEF/PIF)).

The measurement of the above parameters using the present invention has a number of applications. The present invention may be used in determining the effects of environmental particles on the breathing patterns of humans and animals. The present invention may be used in determining toxic effects of gases on human and animal respiration. The present invention may be used in determining the effectiveness of drug delivery (for estimating pharmacokinetics of drugs) to the lungs by measuring respiratory parameters of humans and animals. The present invention may be used in monitoring respiratory parameters of both humans and animals in clinical situations. The present invention may be used in epidemiology studies. The present invention may be used in the study and treatment of sleep apnea. Sleep apnea is marked by an extended expiration period. The normal expiration period for a human is a few seconds. In a person suffering from sleep apnea, the expiration period, during sleep, may be 15 seconds to 2 minutes. The present invention is able to measure this parameter directly and the data acquisition system tracks it.

During development of the present invention, it was used to assess pathophysiologic mechanisms resulting from the exposure to filtered air, residual particles obtained from oil-fired plants (fly ash), or concentrated ambient particles derived from air samples obtained from a typical urban aerosol in Boston, Mass. An ambient air particle concentrator was used that concentrates these particles roughly 30 times to achieve particle concentrations in the range of hundreds of micrograms per cubic meter, without affecting their size or chemical composition. Fully awake dogs were exposed to concentrated ambient air particles or filtered air via tracheostomy, two at a time, for six hours per day on three consecutive days to simulate a particulate air pollution episode. Three exposure protocols were used: 1) One dog was exposed to concentrated ambient air particles, or fly ash particles, while its partner was exposed to filtered air; 2) Both dogs were exposed to concentrated ambient air particles, or fly ash particles; or 3) Both dogs were exposed to filtered air. All dogs went through each of these protocols at least once, thus, all dogs received multiple exposures to concentrated ambient air particles, or fly ash particles. Data comparisons were made between exposures to concentrated ambient air particles or fly ash particles and filtered air for both paired dogs and each individual dog. In addition, the effects of concentrated ambient air particles were determined in animals whose cardiovascular state was compromised by the use of balloon occlusion of the left anterior descending coronary artery to induce myocardial ischemia.

Figure 7A:
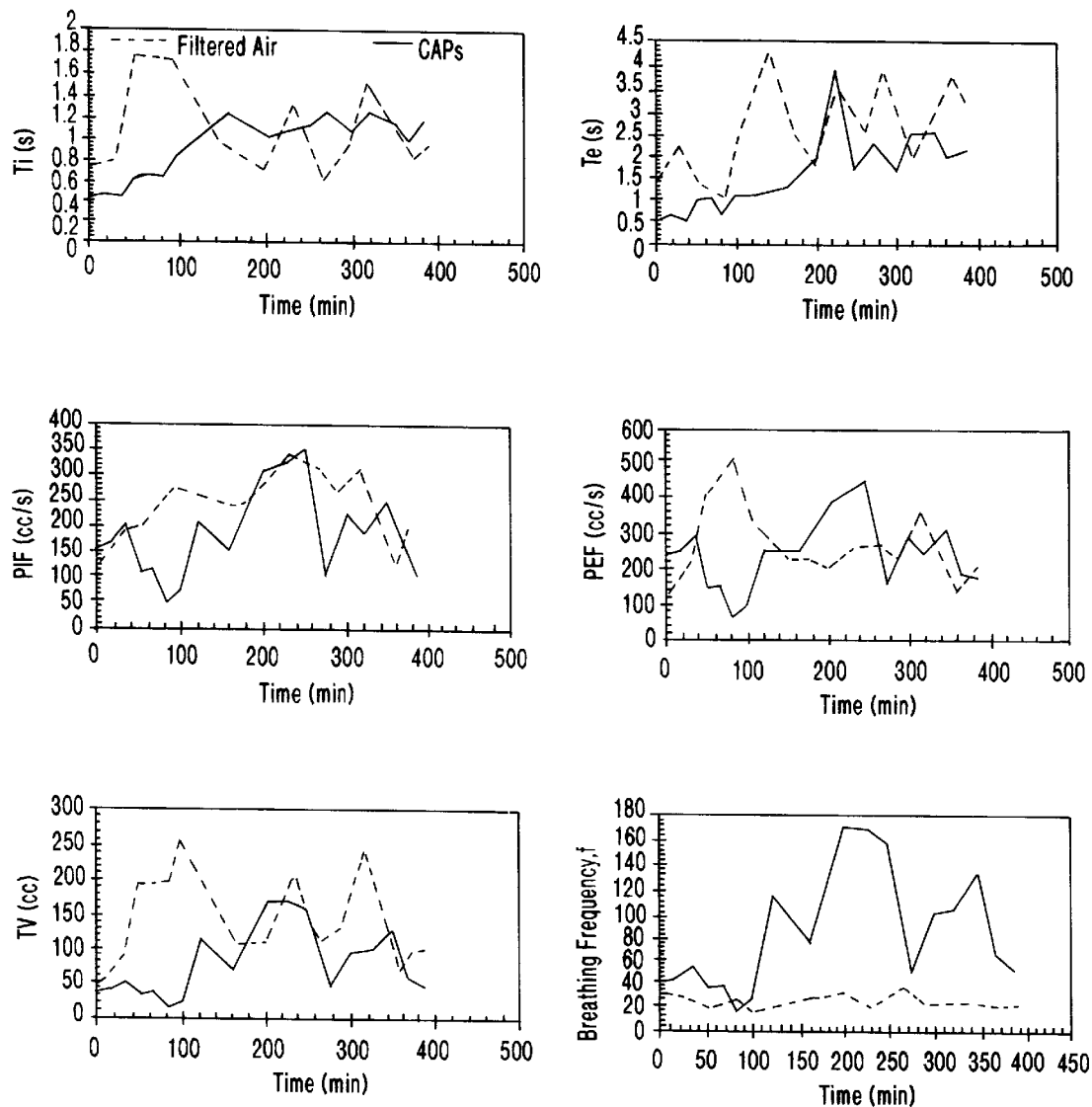
FIGS. 7a and 7b are graphs showing the breathing parameters of normal dogs (over periods averaging 15 minutes) measured as a function of time during exposures to clean air and exposure to the fraction of ambient air particles that are 2.5 microns or less ($PM_{2.5}$)
Figure 7B:
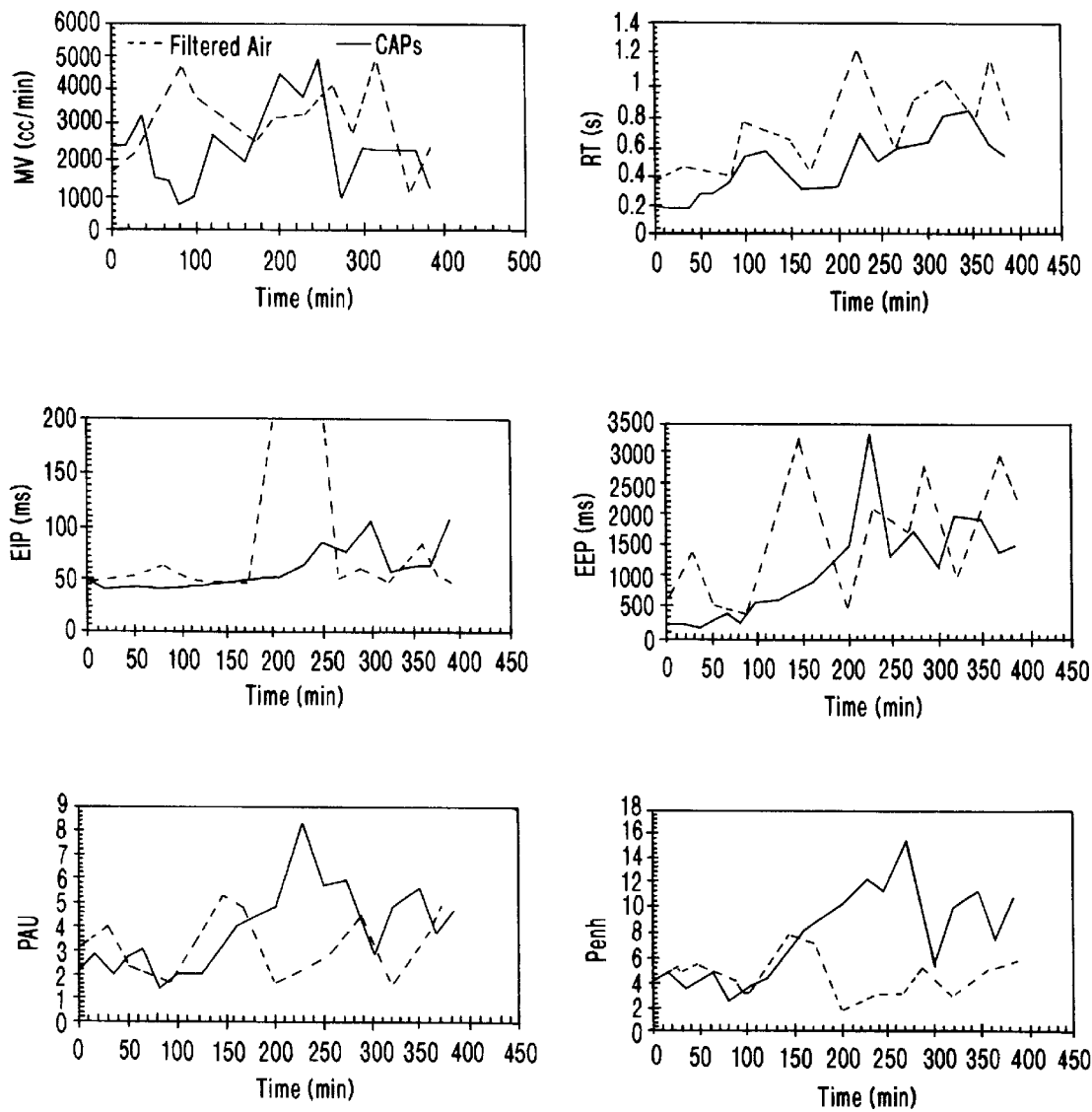

FIGS. 7a and 7b show the breathing parameters of normal dogs (over periods averaging 15 minutes) measured as a function of time during exposures to clean air and exposure to the fraction of ambient air particles that are 2.5 microns or less ($PM_{2.5}$). These measurements on exposed dogs were carried out by monitoring airflow through the tracheostomy tube using the flow restrictor. Each breath throughout the six-hour exposure period is thus available for analysis. A variety of standard respiratory parameters can be measured, in these animals, including but not limited to Respiratory Frequency (f), Tidal Volume (TV), Minute Volume or Ventilation (MV), Peak Inspiratory Flow (PIF), Time for Inspiration ($T_i$), Peak Expiratory Flow (PEF), Time for Expiration ($T_e$), as is indicated in these figures. These measurements indicate the effect of ambient particles on the dogs' breathing parameters. The analysis of the data obtained from several exposure experiments using ambient particles reveal the effects of these particles on the human and animal health.

FIG. 8 shows the respiratory data collected on a normal adult human female subject during the use of the present invention that includes the face mask adaptation. As indicated in the figure, the respiratory parameters measured were Time for Inspiration ($T_i$); Time for Expiration ($T_e$); Peak Inspiratory Flow (PIF); Peak Expiratory Flow (PEF); Tidal Volume (TV); Respiratory Frequency (f); Minute Volume of Ventilation (MV); Relaxation Time (RT), which is defined as the time it takes the expiration volume to decrease to 70 percent of its value as measured using the area under the pressure versus time curve for expiration; End Inspiratory Pause (EIP); End Expiratory Pause (EEP); and Pause (Pau); and enhanced Pause (Penh). These data are shown as two-minute averages with an overall average that includes a standard deviation.

In other alternative embodiments of the invention, the pressure transducer 35 may be placed closer to the flow restrictor 20 in cases where the subject may be able to tolerate the weight of the transducer 35. For instance, a human subject could have the transducer 35 positioned on an upper arm or the flow tubes or the nose piece itself as shown in FIG. 3.

In addition to the advantage of providing precision data for the accurate measurement of a number of pulmonary function parameters, the present invention has the additional benefit of working independently of the position of the subject. The subject can lie down or sit up and move around to a limited extent while measurements are taken. This aspect is particularly useful when performing experiments on conscious animals. An animal that can move and make itself comfortable within the confines of an experiment is less stressed, resulting in more reliable data from the experiment.

Another advantage of the present invention over the whole body plethysmograph is that the present invention, is much smaller and may be used on a patient at bedside, including those who are anesthetized, unconscious, or otherwise non-responsive. So, a patient who is, for example, in intensive care, does not have to be moved in order to gather pulmonary function data. Also, breathing parameters measured using the present invention give a complete set of parameters as compared to the whole body plethsymographs. The breathing parameters measured accurately by whole-body plethysmograph are frequency, pause and enhanced pause. Times for inspiration, expiration and relaxation may be measured less accurately.

Figure 9:
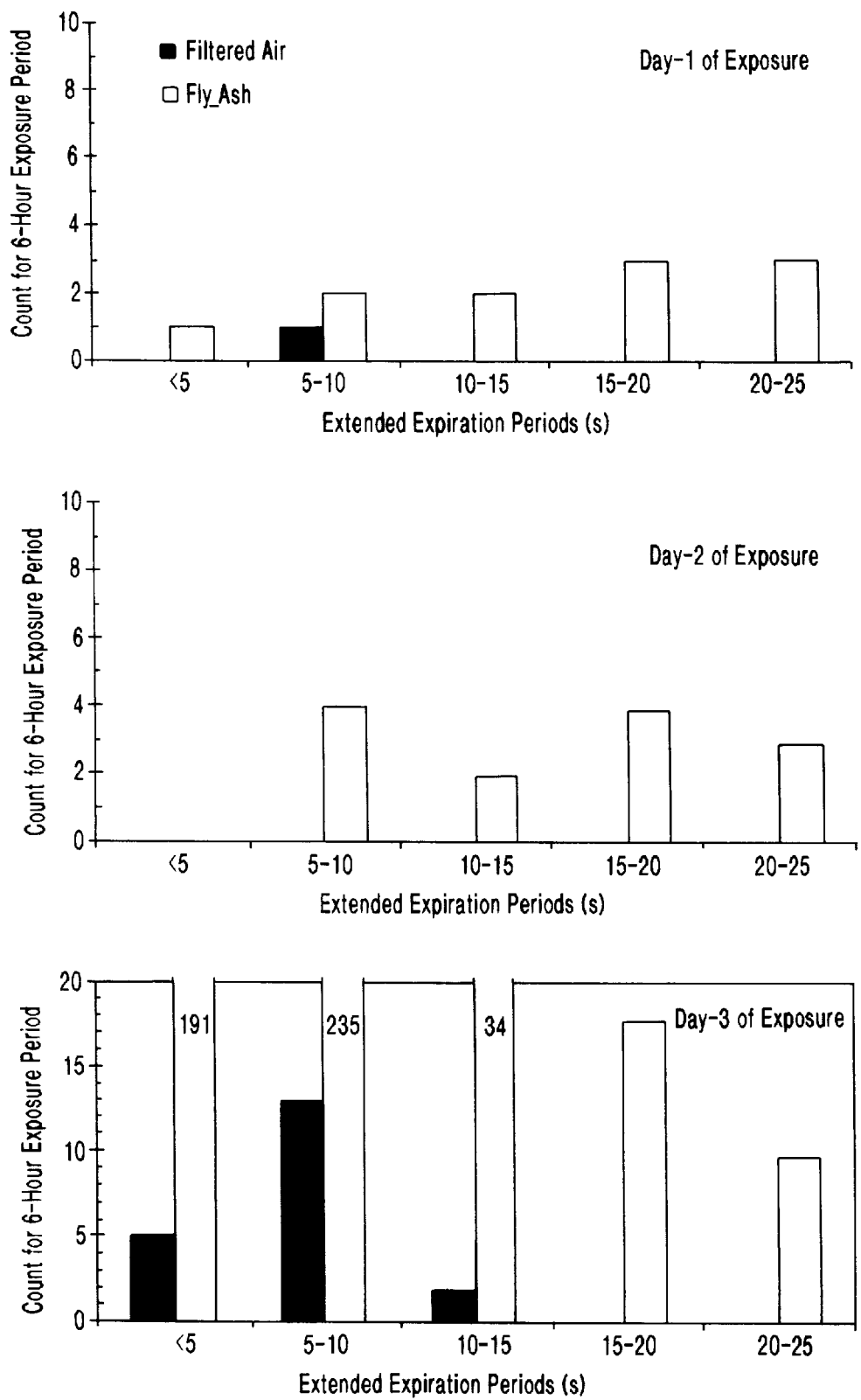

The present invention may also be used in sleep-apnea studies. FIG. 9 shows the results of a series of measurements made on dogs using an embodiment of the present invention. These measurements were made during exposures to filtered-air, concentrated ambient air particles, and fly ash. During the exposures, several breathing parameters were measured including measured expiratory time. The measured expiratory time ($t_e$) values may be used to estimate the apnea episodes in the dogs. The definition for an apnea episode is an expiratory time ($t_e$) which exceeds 15 seconds. For dogs, apnea periods may be defined as an expiratory time ($t_e$) which is 10 seconds or more. FIG. 9 shows the extended expiratory time values (periods>$2t_{e(normal)}$) determined using two dogs exposed to filtered air, and fly ash for 6 hours per day for three days. While the dog exposed to filtered air showed no episodes of apnea during first two days, the dog exposed to fly ash had a number of apnea episodes. On the third day of exposure, the dog exposed to filtered air had 5, 13, and 2 counts of extended expiratory period in the ranges of <5, 5–10, and 10–15 seconds, respectively. The fly ash exposed dog on the third day had 191, 235, 34, 18, and 10 counts of extended expiratory periods in the ranges of <5, 5–10, 10–15, 15–20, and 20–25 s, respectively. These extended expiratory periods were determined from the breath by breath analysis of the dogs breathing pattern measurements using the present invention. A simple algorithm was developed to extract the defined extended expiratory periods from the gathered data. Similar measurements can be made in humans and other animals.

The present invention may also be useful in determining breathing parameters like Forced Expiratory Volume measured for 1 second ($FEV_1$), Forced Vital Capacity (FVC), Functional Residual Capacity (FRC), and Airway Resistance ($R_a$), or any other breathing parameters which may have relevance. These parameters have been used widely in the epidemiological studies. The values for FRC and $R_a$ may be determined using breathing parameters measured using the present invention and the following definitions:

$$FRC = TV/((PEF/PIF)-1)$$

and $$R_a = 2(PEF+PIF)(63.5/ER)t_i t_e / \{\pi TV(t_i+t_e)\}$$

where ER is the Effective Range of volume flow rate measurement for the differential_pressure_transducer-amplifier setup used for the measurements. ER values for the setup used in the measurements for the results shown in FIG. 8 were 1329.83 cc/s. The values of FRC and $R_a$ for the female human subject, estimated using the 30 minutes average values presented in FIG. 8, are 6.75±0.99 liters, and 53.43±5.84 mmH$_2$O/liter/s. These estimated values for the measurements presented in FIG. 8 are roughly in the ranges reported in the literature for normal human subjects.

It is to be understood that the above-described embodiments are simply illustrative of the principles of the invention. Various and other modifications and changes may be made by those skilled in the art which will embody the principles of the invention and fall within the spirit and scope thereof.

What is claimed is:

1. A flow restrictor device for measuring respiratory parameters, comprising:

a respiration-channeling device, said respiration-channeling device having a first preselected diameter and a preselected length;

a flow restrictor having a second preselected diameter positioned inside said respiration-channeling device, said flow restrictor having a first end and a second end;

said first preselected diameter and said preselected length of said respiration-channeling device, and said second preselected diameter of said flow restrictor being selected such that flow within said respiration-channeling device is laminar;

a first pressure sensor positioned adjacent said first end of said flow restrictor for detecting a first pressure;

a second pressure sensor positioned adjacent said second end of said flow restrictor for detecting a second pressure; and a pressure transducer connected to the first pressure sensor and the second pressure sensor, the pressure transducer determining a difference between the first pressure and the second pressure, whereby the difference between the first pressure and the second pressure indicates the volume flow rate of breath in said respiration-channeling device.

2. The flow restrictor device of claim 1 further comprising:
a data acquisition system connected to the pressure transducer for analyzing pressure data to determine volume flow rate of respiration in said respiration-channeling device.

3. The flow restrictor device of claim 2 wherein said data acquisition system derives pulmonary function parameters from the volume flow rate.

4. The flow restrictor device of claim 1 wherein said respiration-channeling device comprises a tracheostomy tube.

5. The flow restrictor device of claim 1 wherein said respiration-channeling device comprises a face mask.

6. The flow restrictor device of claim 1 wherein said respiration-channeling device comprises a mouthpiece.

7. The flow restrictor device of claim 1 further comprising:
a first pressure-sensor tube coupled between said respiration-channeling device and said pressure transducer;
a second pressure-sensor tube coupled between said respiration-channeling device and said pressure transducer,
whereby said respiration-channeling device and said pressure transducer may be separated to operate at a distance from each other.

8. The flow restrictor device of claim 1 wherein the pressure transducer is mounted on the respiration-channeling device.

9. The flow restrictor device of claim 4 wherein the pressure transducer is mounted to an arm of a person using said respiration-channeling device.

10. A method of measuring respiratory parameters, comprising the steps of:
providing a respiration-channeling device, said respiration-channeling device capable of being connected at one end to a breathing subject;
providing a flow restrictor within said respiration-channeling device to produce a laminar flow within said respiration-channeling device;
detecting a first pressure value at a first end of said flow restrictor;
detecting a second pressure value at a second end of said flow restrictor; and
determining from said first pressure value and said second pressure value a volume flow rate of the breath of the subject.

11. The method of claim 10 wherein said determining step includes analyzing the pressure values with a data acquisition system to determine volume flow rate of respiration.

12. The method of claim 11 further comprising the step of:
determining pulmonary function parameters from said volume flow rate with said data acquisition system.

13. The method of claim 10 wherein the providing step further comprises providing a mask for channeling respiration of the breathing subject.

14. The method of claim 10 wherein the providing step further comprises providing a mouthpiece for channeling respiration of the breathing subject.

15. The method of claim 10 wherein the providing step further comprises providing a tracheostomy tube for channeling respiration of the breathing subject.

16. A device for measuring respiratory parameters of a breathing subject, comprising:

a mask for channeling respiration of a breathing subject;
a breathing tube connected to the mask and taking respiration from the mask, said breathing tube having a first preselected diameter and a preselected length;
a flow restrictor positioned inside the breathing tube, the flow restrictor having a first end and a second end and having a second preselected diameter;
said first preselected diameter and said preselected length of said breathing tube, and said second preselected diameter of said flow restrictor being selected such that flow within said breathing tube is laminar;
a first pressure sensor positioned at the first end of the flow restrictor for detecting a first pressure;
a second pressure sensor positioned at the second end of the flow restrictor for detecting a second pressure; and
a pressure transducer connected to the first pressure sensor and the second pressure sensor, the pressure transducer determining a difference between the first pressure and the second pressure,
whereby the difference between the first pressure and the second pressure indicates the volume flow rate of breath of the breathing subject.

17. The device of claim 16 further comprising:
a data acquisition system receiving data from the pressure transducer for analyzing the data to determine volume flow rate of respiration.

18. The device of claim 17 wherein said data acquisition system derives pulmonary function parameters from the volume flow rate.

19. A flow restrictor device for measuring respiratory parameters of a breathing subject, comprising:
a tracheostomy tube attached at one end to the breathing subject, said tracheostomy tube having a first preselected diameter and a preselected length;
a flow restrictor positioned inside the tracheostomy tube, said flow restrictor having a first side and a second side and having a second preselected diameter, said flow restrictor limiting flow through said tracheostomy tube in order to cause a pressure differential between said first side and said second side;
said first preselected diameter and said preselected length of said tracheostomy tube, and said second preselected diameter of said flow restrictor being selected such that flow within said tracheostomy tube is laminar;
a first pressure-sensor tube configured to receive air at said first side of said flow restrictor;
a second pressure-sensor tube configured to receive air at said second side of said flow restrictor;
a pressure transducer coupled to said first pressure-sensor tube and said second pressure-sensor tube; and,
a data acquisition device coupled to said pressure transducer, said data acquisition device determining a breath flow rate of the subject from the pressure differential created by said flow restrictor and detected by said pressure transducers, said data acquisition device deriving pulmonary function parameters for the subject from the breath flow rate.

20. The flow restrictor device of claim 19 further comprising:
a data acquisition system receiving data from the pressure transducer for analyzing the data to determine volume flow rate of respiration.

21. The flow restrictor device of claim 20 wherein said data acquisition system derives pulmonary function parameters from the volume flow rate.

* * * * *